United States Patent [19]

Brain

[11] Patent Number: 5,682,880
[45] Date of Patent: Nov. 4, 1997

[54] LARYNGEAL-MASK AIRWAY WITH GUIDE ELEMENT, STIFFENER, AND FIBEROPTIC ACCESS

[76] Inventor: Archibald Ian Jeremy Brain, Sandford House, Fan Court Gardens, Longcross Road, Chertsey, Surrey, England, KT16 ODJ

[21] Appl. No.: 690,351

[22] Filed: Jul. 26, 1996

Related U.S. Application Data

[63] Continuation-in-part of PCT/GB95/01292, Jun. 5, 1995.

[51] Int. Cl.[6] .................. A61M 16/00; A61M 5/178; A61M 25/00; A61M 5/32
[52] U.S. Cl. ........................ 128/207.15; 128/200.26; 128/207.14; 604/174; 604/96; 604/164; 604/282
[58] Field of Search ............... 128/200.26, 207.14, 128/207.15, 911; 604/174, 96, 164, 282

[56] References Cited

U.S. PATENT DOCUMENTS

| | | | |
|---|---|---|---|
| 3,774,616 | 11/1973 | White et al. | 128/200.26 |
| 4,672,960 | 6/1987 | Frankel | 128/200.26 |
| 4,976,261 | 12/1990 | Gluck et al. | 128/207.15 |
| 5,285,778 | 2/1994 | Mackin | 128/207.15 |
| 5,303,697 | 4/1994 | Brain | 128/200.26 |
| 5,339,805 | 8/1994 | Parker | 128/200.26 |
| 5,477,851 | 12/1995 | Callaghan et al. | 128/207.15 |
| 5,507,279 | 4/1996 | Fortune et al. | 128/200.26 |

FOREIGN PATENT DOCUMENTS

| | | |
|---|---|---|
| WO 91/07201 | 5/1991 | WIPO . |
| WO 92/13587 | 8/1992 | WIPO . |

Primary Examiner—Kimberly L. Asher
Attorney, Agent, or Firm—Hopgood, Calimafde, Kalil & Judlowe

[57] ABSTRACT

An intubating laryngeal-mask airway device compresses a flexible airway tube with conventional distal-end mask structure, wherein one or more relatively stiff and suitably curved reinforcement elements determine the curvilinear course of the airway tube and are removably embodied in the flexible airway tube. An external handle connected to the proximal end of the one or more reinforcement elements facilitates rapid installation of the mask, and removal of the one or more reinforcement elements exposes guide passages well suited to subsequent introduction of fiber-optic devices for visual inspection of the entrance to the trachea, whereby to assure properly directed passage of an endotracheal tube or other instrumentation into the trachea. Optional provision is made for use of a reinforcement-guide system to serve another fiber-optic device having viewing exposure directed toward the oesophagus, thereby providing a visible clue of a misdirected endotracheal tube before it can do any damage in a region which must be avoided.

22 Claims, 2 Drawing Sheets

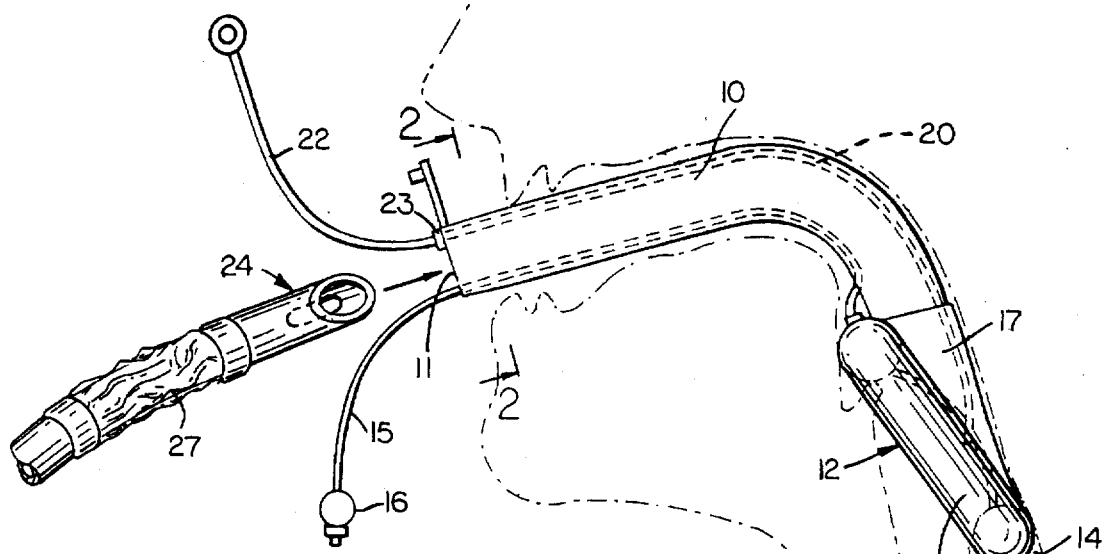
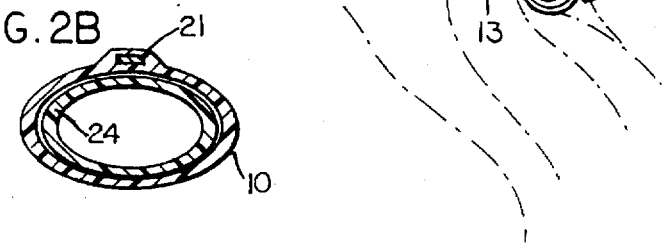
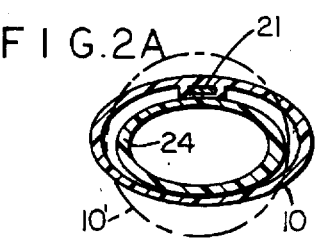
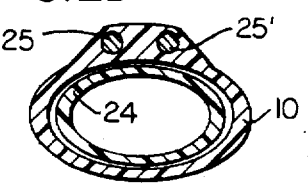
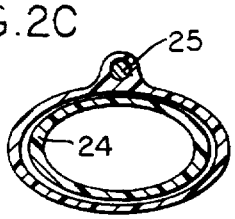
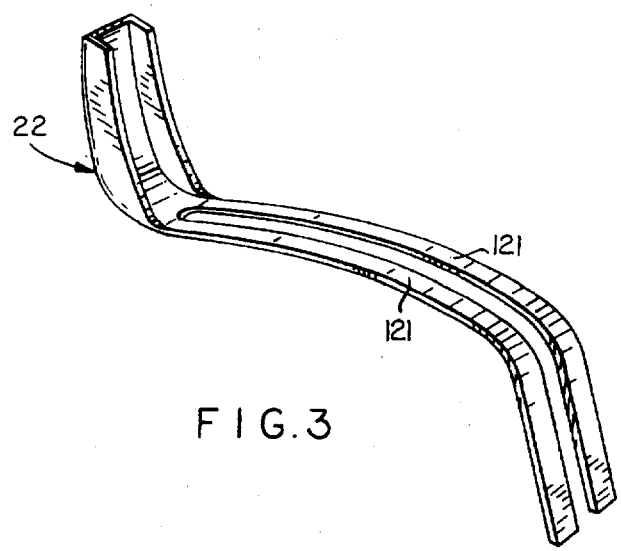

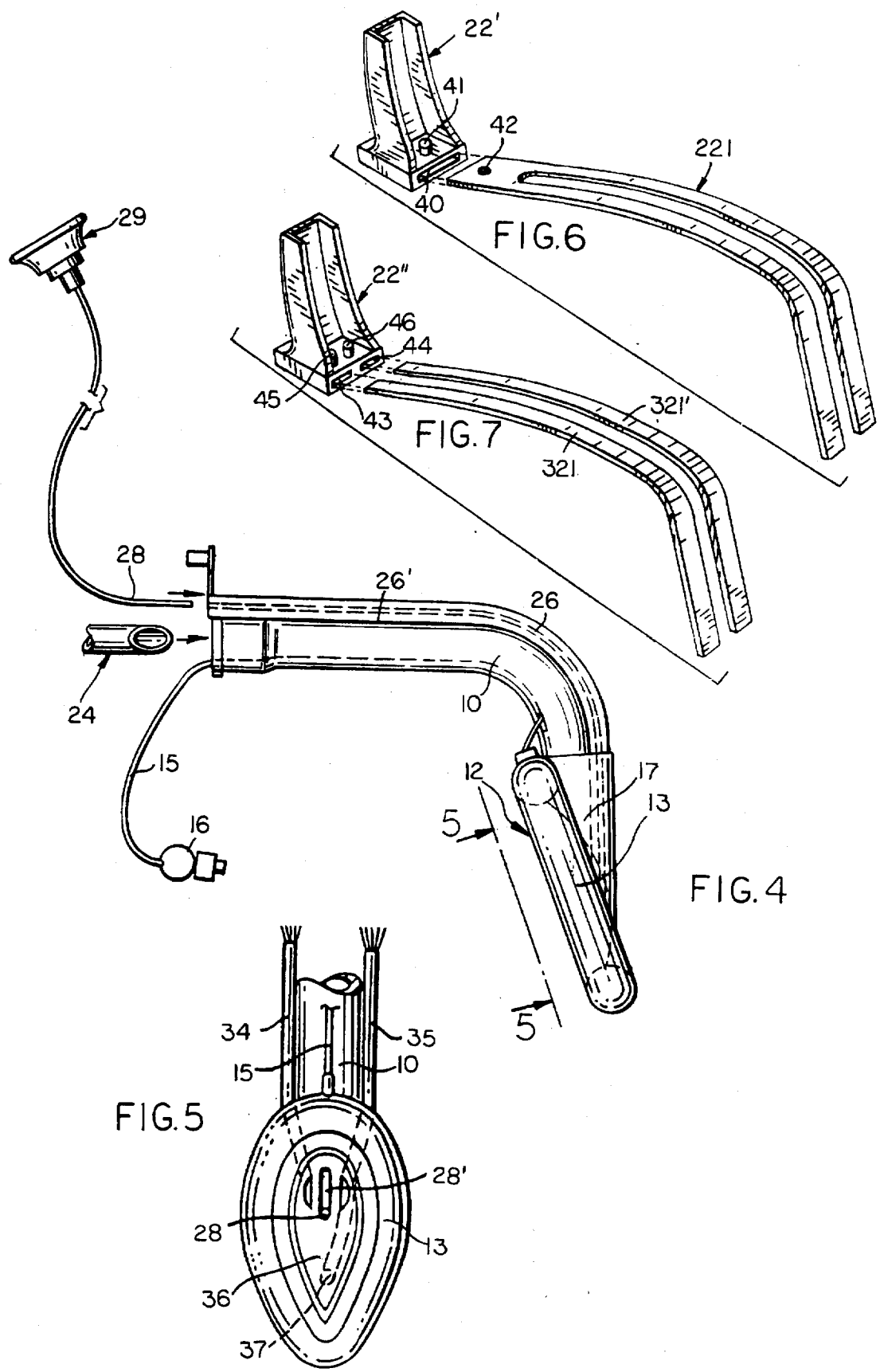

LARYNGEAL-MASK AIRWAY WITH GUIDE ELEMENT, STIFFENER, AND FIBEROPTIC ACCESS

RELATED CASE

This application is a continuation-in-part of PCT/GB95/01292, filed Jun. 5, 1995, with designation of the United States for National Phase prosecution.

BACKGROUND OF THE INVENTION

This invention relates to a fibreoptic intubating laryngeal-mask airway device for use in anaesthesia.

Laryngeal-mask airway devices are described in British Patents 2,111,394 (corresponding to U.S. Pat. No. 4,509,514) and 2,205,499 and in a number of corresponding foreign patents and patent applications.

Despite the success of such laryngeal-mask airway devices, which are now used in some 40 percent of all anaesthetic procedures in the United Kingdom, intubation of the trachea remains the ultimate objective of airway management in an emergency or when there may be a risk of inhalation of gastric contents, since the presence of a cuffed tube in the trachea prevents gastric acid present in vomit from entering and damaging the lungs. However, intubation of the trachea is not always possible and, when difficulty is experienced, soiling of the lungs with gastric acid may occur while attempts are being made to intubate.

The laryngeal-mask airway as described in the above patents has been modified by using a thin-walled rigid tube, with external manipulating handle, as described in British patent 2,252,502 (corresponding to U.S. Pat. No. 5,303,697), in order to facilitate intubation of the trachea, using the laryngeal-mask airway as a guide for insertion of an endotracheal tube; such laryngeal-mask devices have been called intubating laryngeal masks. The rigid tube with manipulating handle not only enables an operator to make a rapid insertion, without having to reach into the patient's mouth, but also makes it possible to accommodate an endotracheal tube which may be characterized by one of a variety of tube diameters. Rapid insertion is of utmost importance because delay in providing an airway to the trachea can have fatal consequences.

Use of a rigid airway tube, as in the structures of said U.S. Pat. No. 5,303,697 is good from the point of view of ease of external manipulation, but there are cases in which the patient may be suffering from a trauma condition wherein his jaws are so locked as to prevent entry of the rigid tube between teeth of his jaws. Also, certain patients may have unusual pharyngeal and other configurations that make a mask at the distal end Of a rigid airway tube less than best suited for sealed engagement to the patient's laryngeal inlet.

BRIEF STATEMENT OF THE INVENTION

It is an object of the invention to provide an improved laryngeal-mask configuration with features of intubating guidance, wherein above-noted difficulties are avoided or reduced.

It is a specific object to meet the above object with an airway tube that is basically relatively flexible but is reinforced to an extent permitting rapid handle-manipulated distal placement of a laryngeal mask in sealed relation to a patient's laryngeal inlet.

Another specific object is to provide a laryngeal mask meeting the above objects and permitting selective removal of the reinforcement, once the mask has been installed, so that basic flexibility of the airway tube can permit more tolerable self-adaptation to wall features of the patient's airway to the pharynx.

A further specific object is to meet the above objects with a construction which additionally provides guidance for a fiber-optic endoscopic device so that an operating technician can observe the distal end of an endotracheal tube in the course of its proper advance through the mask and into the patient's trachea, thus avoiding accidental passage of the endotracheal tube into the oesophagus.

The invention achieves these objects by providing a flexible airway tube with conventional distal-end mask structure, wherein one or more relatively stiff and suitably curved reinforcement elements determine the curvilinear course of the airway tube and are removably embodied in the flexible airway tube. An external handle connected to the proximal end of the one or more reinforcement elements facilitates rapid installation of the mask, and removal of the one or more reinforcement elements exposes guide passages well suited to subsequent introduction of fiber-optic devices for visual inspection of the entrance to the trachea, whereby to assure properly directed passage of an endotracheal tube or other instrumentation into the trachea. Optional provision is made for use of a reinforcement-guide system to serve another fiber-optic device having viewing exposure directed toward the oesophagus, thereby providing a visible clue of a misdirected endotracheal tube before it can do any damage in a region which must be avoided.

BRIEF DESCRIPTION OF THE DRAWINGS

In the drawings, which show for illustrative purposes preferred structures of the invention:

FIG. 1 is a simplified view in side elevation, showing a laryngeal-mask assembly of the invention, installed in a patient and poised to receive and guide an endotracheal tube for safe entry into the trachea of a patient;

FIG. 2A is an enlarged view in cross-section taken at 2—2 in FIG. 1, to show a compressionally distorted airway tube and inserted endotracheal tube;

FIG. 2B is a view similar to FIG. 2A, for a first-modification;

FIG. 2C is another view similar to FIG. 2A, for a second modification;

FIG. 2D is also a view similar to FIG. 2A, for a third modification;

FIG. 2E is another view similar to FIG. 2A, for a fourth modification;

FIG. 2F is a further view similar to FIG. 2A, for a fifth modification;

FIG. 3 is a simplified view in perspective, for reinforcement structure contained in the assembly of FIG. 1, when the section at 2—2 is as depicted in FIG. 2E or FIG. 2F;

FIG. 4 is a view similar to FIG. 1, for a further modification;

FIG. 5 is a plan view of the inflated side of the laryngeal mask of FIG. 4, namely, the side that is adapted for sealing engagement to the laryngeal inlet of a patient, the same being as viewed from the aspect 5—5 of FIG. 4;

FIG. 6 is a view as in FIG. 3, for a first modification thereof; and

FIG. 7 is another view as in FIG. 3, for a second modification thereof.

DETAILED DESCRIPTION

In FIG. 1, a laryngeal-mask device of the invention is seen to comprise an airway tube 10 of sufficiently flexible nature to adapt comfortably to a path of airway supply from an externally accessible proximal end 11 outside a patient's mouth to a distal end 12 of peripherally sealed masking fit to the patient's laryngeal inlet. Distal-end masking structure at 12 comprises an inflatable ring 13 of generally elliptical configuration, the same being shown located distally at the oesophageal inlet 14 and generally contained with the pharyngeal cavity. As explained in the prior patents identified above, the mask assembly 10,12 is installed in the deflated state of ring 13, and inflation is via an external air tube 15 and associated check-valve 16, to complete the installation; the mask assembly 10,12 is later removed after deflating (evacuating) ring 13 via tube 15 and its check valve 16. The inflatable ring 13 surrounds a mask aperture within a backing plate 17 for exclusive airway (10) communication to the trachea of the patient.

In accordance with a feature of the invention, a continuous guide passage 20 of limited section area accommodates a reinforcing member 21 (see FIG. 2A) which stiffens the airway tube 10 for purposes of laryngeal-mask installation and externally driven manipulation via a handle formation 22 at the proximal end of the reinforcing member 21. Illustratively, a collar or shoulder formation 23, at juncture of handle 22 to member 21, abuts the proximal end of tube 10 to limit the extent of member 21 accommodation in passage 20. The reinforcing member 21, as seen in FIG. 2A, is of relatively stiff material such as surgical stainless steel, and of rectangular section wherein the width or greater dimension of the section exceeds the thickness dimension and is oriented by guide passage 20, so as to be somewhat tangential to the generally circular section profile of tube 10 in its unstressed state, schematically suggested by phantom outline 10' in FIG. 2A. Preferably, the material of reinforcement member is sufficiently ductile or malleable at room temperature as to permit a medical technician to manually pre-bend and thus to adjust the curvature of tube 10 as in his judgment will best adapt to the individual patient; such pre-bending adjustability may, for example, be important for service of a patient afflicted with rheumatoid arthritis. Once the mask is installed and inflated to seal its engagement to and around the laryngeal inlet, the reinforcement member 21 has served its purpose, and handle 22 conveniently aids manual application of extraction force with one hand, while the other hand is applied to the proximal end 11 of the airway tube 10 so as not to dislodge or impair sealing effectiveness at the laryngeal inlet. It is to be noted that use of handle 22 enables a rapid and effective installation of the mask 12 and that, once inflated to establish the sealed engagement, the patient has a sealed airway passage to the lungs, and any risk of gastric-product access to the trachea has been avoided.

Once the laryngeal-inlet seal has been established by inflation of ring 13, the critical urgency of time no longer exists, so that the anaesthetist or medical technician is not under life-threatening pressure to install the desired endotracheal tube, which will be understood to be schematically suggested by the distal end of tube 24 in FIG. 1. He has the option to perform the intubation with or without the reinforcing member 21. If member 21 remains in place until after intubation is completed, with the endotracheal cuff 27 inflated to assure that the trachea is sealed from gastric intrusion or contamination, then the existence of reinforcement member 21 at the outer radius of airway-tube curvature will provide a measure of enhanced smoothly guided endotracheal-tube guidance through such curvature, in the insertional course of the intubation process. If on the other hand, handle 22 and its reinforcement member 21 have been removed prior to commencement of intubation, the passage 20, vacated by removal of the reinforcement member, is available for guided entry of a fibreoptic scoping device, not shown in FIG. 1 but schematically suggested at 28 in FIG. 4, with ocular means 29 to view through a mask aperture 28' (FIG. 5), prior to insertion of the endotracheal tube 24. Having thus first inserted the distal end of the scoping device 28 to the point of trachea viewing through a mask opening 28', the endotracheal tube 24 may next be inserted and endoscopically verified for intubating entry into the trachea.

The diagrams of FIGS. 2B to 2F merely illustrate alternative section configurations of the airway tube 10 thus, in FIG. 2A, the provision for guided fit of the reinforcement member 21 is an integral formation with the inner wall of tube 10; and in FIG. 2B, such a guided fit is an integral formation with the outer wall of tube 10. In FIG. 2C, the reinforcement member 25 is a rod of circular section which may have been preassembled to an annular sheath 26 of elastomeric material (as in FIG. 4), prior to adhesively bonded connection of the sheath at 26' to airway tube 10; in the form shown in FIG. 2C, however, the reinforcement rod 25 has slidable guided accommodation in a guide passage of circular section, which is suitably a product of having extruded a suitable elastomeric material, such as silicone rubber, to form tube 10, complete with the formed guide passage for rod 25.

In FIG. 2D, the reinforcement rod 25 is one of two (25,25') of like nature, each of which has its own guide passage, the same being in spaced parallel relation throughout the length of the airway tube. Preferably, the same single handle 22 serves for manipulating both of the rods 25,25' with mutually cooperating effectiveness.

FIGS. 2E and 2F illustrate formation of dual spaced passages 30 (FIG. 2E) and 31 (FIG. 2F) in the airway tube 10, respectively as inner-wall formations and outer-wall formations. In either event, FIG. 3 illustrates two reinforcement members 121 of like rectangular section united to the same manipulating handle 22, and suitable for accommodation in the respective passages 30 of FIG. 2E or 31 of FIG. 2F.

Recalling that airway tube 10 is initially of circular profile 10' and that it is also compliantly compressible, as if the case with commercially available endotracheal tubes, such as tube 24, FIGS. 2A to 2F serve further to illustrate that, as compared with the rigid intubating airway tubes of U.S. Pat. No. 5,303,697, both the present airway tube (10) and the endotracheal tube (24) which it must accommodate are similarly compressible, as to the elliptical configurations shown for FIGS. 2A to 2F. That being the case, a substantial measure of compliant diametric compression is available in reduction of the jaw-opening requirements, for difficulties often encountered in attempted intubation of a patient in shock. In no way is the elliptically distorted airway tube impaired in its ability to provide adequate air to the patient, even though the endotracheal tube may also be elliptically distorted at passage through the patient's jaws.

FIG. 5 further serves to illustrate that in the event of dual-passage provision for removable reinforcement members, as in FIGS. 2D, 2E, and 2F, the fibre-optic lines 34,35 of two endoscopic viewing systems can be individually served by the respective guide passages which are vacated upon removal of the involved reinforcement members. And it will be understood that these guide passages may direct the respective fibre-optic lines through spaced aperture regions 34',35' of the mask, to provide two independently viewable aspects on the trachea, or to provide for binocular (i.e., stereoscopic) viewing. Alternatively, one of the guide passages may serve for viewing trachea via a mask aperture, and the other passage may serve for viewing the distal region of the mask membrane 36 via a localized distal opening 37 through the membrane 36, thereby enabling the technician to stop further in-feed of the endotracheal tube 24, in the event that the distal end of tube 24 is seen to veer and from its intended course to the trachea and threatens to enter the oesophagus.

It has been indicated that the reinforcement member or members may be of rectangular section wherein width exceeds thickness; preferably, for such a section, the width may advantageously be in the range of twice to ten times the thickness dimension, which at the last-stated limit may involve a thickness one millimeter and a width of one-half to one centimeter.

Because the airway tube 10 and the endotracheal tube (24) are to a degree (e.g., at least 2.5 percent) compressible without jeopardizing airway communication to the patient, the described construction lends itself to structures wherein the unstressed inner diameter of airway tube 10 may be greater than heretofore, as for example, the 13 mm or 14 mm inner diameter that has characterized the rigid tubular airway of an intubating laryngeal mask, as in the above-mentioned U.S. Pat. No. 5,303,697. Such a bore size for the present airway tube 10 will readily accommodate present commercial endotracheal tubes (with inflatable cuffs) having inner diameters of 6 mm or 8 mm, for which a 2-mm additional allowance can be assumed for tube thickness and for the inflatable cuff 27 of these conventional tube sizes.

And it is further to be noted that for the ophthalmic surgeon who must operate on the eyes of an intubated patient, it is a matter of great convenience to have been able to remove handle 22 and its reinforcement member or members, thereby gaining substantial access for operation upon one or both eyes.

FIGS. 6 and 7 are directed to modifications of FIG. 3, wherein the convenience for an ophthalmic or other operation provides alternative options. In FIG. 6, for example, a single two-tyne reinforcement member 221 is a separate part having detachable selective connection to a handle 22' which is another separate part; the means of detachable connection is seen as a slot formation 40 in the base of the handle, for insertable reception of the flat generally rectangular proximal end of member 221, and means for selective connection and release from connection is schematically indicated at 41,42. With the construction of FIG. 6, it is thus possible to retain the reinforcement afforded by both tynes of part 221, while the handle 22' has been detached for better operational access as may be needed to operate upon the patient's head. Yet the handle can be again connected to reinforcement 221, should removal of the reinforcement 221 later be desired.

In the arrangement of FIG. 7, a handle 22" is again a separate part, and each of two-like reinforcement members 321,321' is a separate part. The base of handle 22" has two parallel slot formations 43,44, for insertable reception of the respective proximal ends of the two reinforcement members, and separate means for selective connection and release from connection are schematically indicated at 45 and 46 respectively. With the construction of FIG. 7, one is thus not only presented with the options mentioned above for FIG. 6, but it is also possible to remove a selected one to the exclusion of the other reinforcement member for what may serve the physician's better procedural judgment.

What is claimed is:

1. A laryngeal mask airway device to facilitate lung ventilation in a patient, comprising an airway tube extending between a proximal end that is adapted for external ventilation and a distal end that is adapted for exclusive communication with the trachea, said distal end comprising a mask having an airway opening to said tube and having a surrounding annular peripheral formation of roughly elliptical shape, said peripheral formation being capable of readily fitting within the pharynx behind the larynx so as to enable the annular peripheral formation to form a seal around the laryngeal inlet without penetration of the device into the trachea, the airway tube being relatively flexible and curved to follow the airway of the patient, the device further comprising an elongate guide along the airway tube, and an elongate relatively stiff reinforcing member removably fitted to said guide, said reinforcing member being in curved conformance to the curve of the airway tube and extending distally to said mask and extending proximally beyond said guide for external manipulation of said device in the patient.

2. The device of claim 1, in which said guide is a continuous passage formation in said tube.

3. The device of claim 2, in which the continuous passage formation is of substantially uniform circular section, and in which said reinforcing member is of similar section and conforms to the curve of the airway tube.

4. The device of claim 2, in which the continuous passage formation is of substantially uniform generally rectangular section having a major section dimension which exceeds an orthogonally related minor section dimension, the orientation of the major section dimension being substantially tangent to the outer convex profile of the curve of the airway tube, and said reinforcing member being of similar section and conforming to the curve of the airway tube.

5. The device of claim 4, in which the major section dimension has a relationship to the minor section dimension, in a range from 2:1 to 10:1.

6. The device of claim 4, in which the material of said reinforcing member is surgical stainless steel.

7. The device of claim 2, in which said reinforcing member is sufficiently malleable to enable a manually bent modification of the curve of the reinforced airway tube prior to inserted installation of the mask airway device in the patient.

8. The device of claim 1, in which said guide is one of two spaced continuous passage formations in said tube, and in which said reinforcing member is one of two, each reinforcing member being removably fitted in one to the exclusion of the other of said passages, and a single manipulating handle connecting the proximal ends of said members to each other.

9. The device of claim 8, in which at least one of said passages has an open distal end that is aligned with the airway opening of said mask, whereby once the device has been installed in a patient, the manipulating handle and its two reinforcing members may be withdrawn from the device, leaving said at least one passage open for accommodating guided insertional reception of a scoping device.

10. The device of claim 9, in which the airway opening of said mask includes two spaced openings, and in which each guide passage has an open distal end that is aligned with a different one of said spaced openings, whereby once the device has been installed in a patient, and the manipulating handle and its reinforcing members have been withdrawn, separate scoping devices may be inserted in the respective guides to view the patient's glottis via the spaced distal ends of the respective scoping devices.

11. The device of claim 10, in which said scoping devices are adapted for binocular viewing of the patient's glottis.

12. The device of claim 1, in which the surrounding annular peripheral formation of the mask is an inflatable ring.

13. The device of claim 1, in which the proximal end of said reinforcing member includes a manipulating handle formation.

14. The device of claim 13, in which said manipulating-handle formation is releasably connectable to said reinforcing member.

15. A kit comprising the device of claim 2, and an elongate flexible scoping device sized for insertional guidance by said guide passage after a removal of said reinforcing member.

16. A laryngeal mask airway device to facilitate lung ventilation in a patient, comprising an airway tube extending between a proximal end that is adapted for external ventilation and a distal end that is adapted for exclusive communication with the trachea, said distal end comprising a mask having at least two spaced airway openings to said tube and having a surrounding annular peripheral formation of roughly elliptical shape and being capable of readily fitting within the pharynx and behind the larynx so as to enable the annular peripheral formation to form a seal around the laryngeal inlet without penetration of the device into the trachea, the airway tube being relatively flexible and curved to follow the airway of the patient, the device further comprising two separate continuous guide passages along said airway tube and in peripherally spaced relation, said guide passages being proximally open at the proximal end of said tube and being distally open at said mask and being respectively adapted for spaced directional alignment with a different one of the two spaced airway openings of said mask, and separate relatively stiff reinforcing members removably fitted to the respective guide passages, each reinforcing member extending distally to said mask and extending proximally beyond its guide for external manipulation of the device in a patient.

17. The device of claim 16, in which the proximal ends of said reinforcing members are connected to a single manipulating-handle formation.

18. The device of claim 17, in which said manipulating-handle formation is releasably connectable to one to the exclusion of the other of said reinforcing members.

19. The device of claim 17, in which said manipulating-handle formation is releasably connectable to both of said reinforcing members.

20. A kit comprising the device of claim 16, and at least one elongate flexible scoping device sized for selective insertional guidance by either of the respective guide passages after a removal of the reinforcing members.

21. A kit comprising the device of claim 16, and two elongate flexible scoping devices sized for insertional guidance by the respective guide passages after a removal of the reinforcing members.

22. The kit of claim 21, further including binocular-viewing means adapted for connection to the proximal ends of the two scoping devices for binocular viewing through said scoping devices.

* * * * *